United States Patent
Heil, Jr. et al.

[11] Patent Number: 5,314,462
[45] Date of Patent: May 24, 1994

[54] POSITIVE FIXATION DEVICE

[75] Inventors: Ronald W. Heil, Jr., Roseville; Wickham, Jr. Robert W., Harris; Bruce H. Kenknight, Robbinsdale, all of Minn.

[73] Assignee: Cardiac Pacemakers, Inc., St. Paul, Minn.

[21] Appl. No.: 888,492

[22] Filed: May 27, 1992

[51] Int. Cl.⁵ ............................................... A61N 1/00
[52] U.S. Cl. .................................................. 607/128
[58] Field of Search ............ 128/784, 785, 786, 419 P, 128/642; 607/119, 122, 123, 125, 126, 127, 128, 130

[56] References Cited

U.S. PATENT DOCUMENTS

| | | | |
|---|---|---|---|
| H356 | 11/1987 | Stokes et al. | 128/419 P X |
| 3,580,242 | 1/1968 | LaCroix | 128/642 |
| 3,844,292 | 10/1974 | Bolduc | 128/419 P X |
| 4,624,265 | 11/1986 | Grassi | 128/784 |
| 4,860,769 | 8/1989 | Fogarty et al. | 128/786 |
| 4,865,037 | 9/1989 | Chin et al. | 128/786 X |
| 5,007,436 | 4/1991 | Smits | 128/786 |
| 5,052,407 | 10/1991 | Hauser et al. | 128/786 |

*Primary Examiner*—Lee S. Cohen
*Assistant Examiner*—Jeffrey R. Jastrzab
*Attorney, Agent, or Firm*—Keck, Mahin & Cate

[57] ABSTRACT

An implantable defibrillation electrode including a conductive distal end portion and a non-conductive proximal end portion is provided with at least a major portion of the length of the distal end portion having a preconfigured shape and being resiliently deformable into a generally straight condition. The distal end portion includes distal and proximal ends and at least one of those ends is hollow and has hook structure shiftably supported therein for movement longitudinally thereof from a retracted position at least substantially contained within the hollow end and an extended position at least substantially fully outwardly projected from the hollow end. Spring structure is provided for yieldingly biasing the hook structure from the extended position toward the retracted position and axial thrust developing structure is slidingly telescoped through the proximal end portion and operatively associated with the hook structure for exerting an axial thrust thereon from the terminal end of the proximal end portion in order to effect shifting of the hook structure from the retracted position to the extended position.

8 Claims, 5 Drawing Sheets

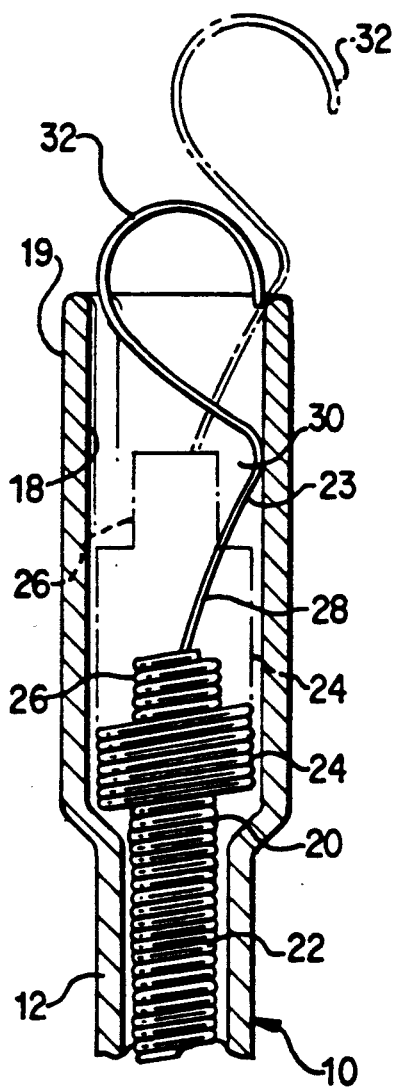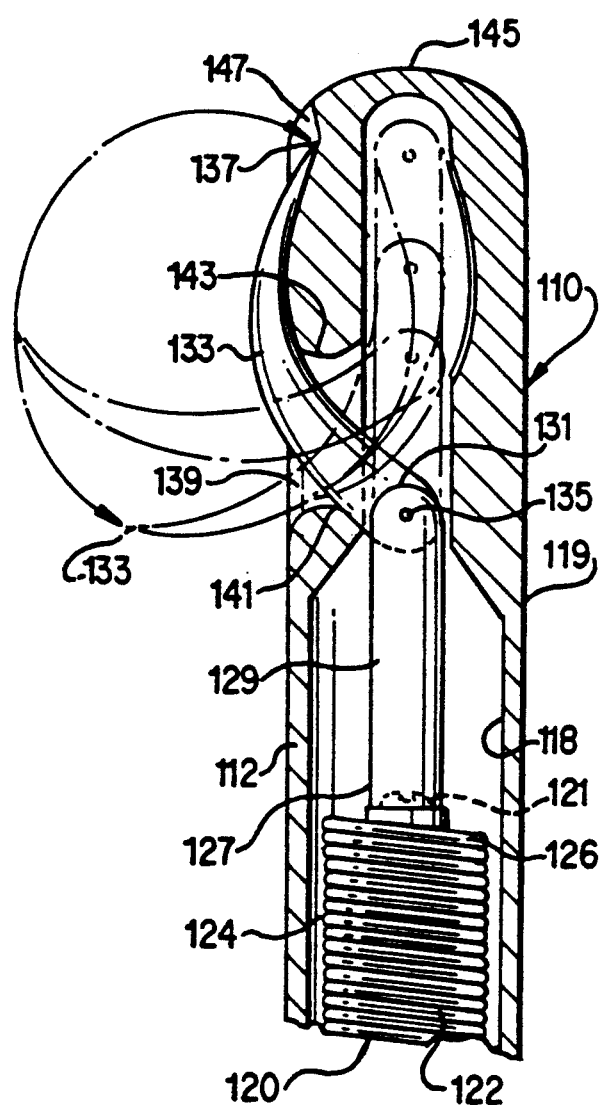
FIG. 1
FIG. 5

POSITIVE FIXATION DEVICE

BACKGROUND OF THE INVENTION

1. Field of the Invention

This invention relates to implantable defibrillation and pacing leads and more particularly to devices of this type which employ fixation structure operative to engage and draw tissue laterally toward the distal end of the defibrillation or pacing lead.

The instant fixation devices are appropriate for minimally invasive defibrillation and use with new, deployable defibrillation leads which are implanted without the currently practiced thoracotomy procedures. The implantation of these leads requires making a small incision in the chest to gain access to the pericardial space. The defibrillation leads are then threaded through the incision and into the pericardial space either alone or through the lumen of a thin walled guiding catheter. Once initially placed in his fashion, a deployment action is performed to expand the surface area of the lead. At this point, the lead is generally held against the myocardial surface by the pericardium.

Because of the lubricious conditions which exist within that space, and the need to more precisely position the leads for defibrillation, lead fixation is required. Fixation to the pericardial sack is the safest approach since it completely avoids accidental laceration of the myocardial circulation. For additional safety, the instant fixation device utilizes hooks that penetrate through the pericardium and return to the lead. These designs do not leave a sharp, pointed object imbedded in the tissue. Still further, the fixation means needs to be robust in order to remain effective through the violent contractions experienced by the heart during initial defibrillation testing. Also, the ability to control device fixation using only simple axial, back-and-forth, "camera cable release-like" motions on common, off-the-shelf devices such as guidewires and stylets is highly desired. This is due, in part, to the fact that the lead may be partially or completely deployed and that lead body rotation and traction due to the remoteness of the insertion site may not be useful technique at this stage of the implant. It also should be noted that although the instant focus is pericardial fixation, these same fixation concepts can be applied to myocardial tissue if knowledge of the local circulation is accurate.

2. Description of Related Art

Various different forms of implantable and internally deployable defibrillation electrodes heretofore have been provided as well as hook and screw-type fixation devices for electrocatheters.

An internally deployable defibrillator electrode is disclosed in U.S. Pat. No. 4,860,760, but does not include structure for fixation prior to or subsequent to deployment of the electrode. U.S. Pat. No. 4,567,900 also discloses an internally deployable defibrillator electrode, but here again also is absent fixation structure.

U.S. Pat. No. 4,624,265 employs both rotary hook and rotary screw fixation devices for an electrocatheter, but rotary hook and rotary screw fixation devices which must be actuated by rotary torque applied at the proximal end of the electro-catheter are objectionable and, this patent does not disclose rotary hook or screw fixation devices which may be utilized in conjunction with an internally deployable defibrillator electrode.

U.S. Pat. No. 3,814,104 describes a pacemaker lead which attaches to endocardial tissue by means of two gently curved hooks advanced from the lead by means of axial force applied by an internal stylet. The essentially straight hooks provide some degree of fixation but can allow the lead to be simply pulled from the tissue. Also, a special separate flexible catheter is required to force the hooks together if the device needs to be repositioned.

It is felt that the violent contraction of the heart which results from a defibrillation shock may cause the dislodgement of this or any easily removable lead. The need for additional, special hardware for repositioning is also unattractive.

U.S. Pat. No. 4,058,128 describes a pacemaker lead which attaches to the myocardium by means of a single, completely exposed barbed hook. At implant, a significant chest incision is performed to expose the pericardial surface, the lead is grasped with a special grasping tool, both the lead and grasping tool are introduced through the relatively large incision (compared to the lead body itself), the barbed hook is inserted into the myocardial tissue and the grasping tool is removed. In the event that repositioning is required, reintroduction of the grasper is necessary to reverse and then repeat the process.

It is felt that the surgical incision, and the need to introduce a grasping tool into the body, fail to adhere to the concept of a minimally invasive lead. Furthermore, a barb feature on this or any hook may also cause local tissue damage as a result of the violent contraction following the delivery of a defibrillation shock. Accidental laceration of the myocardial circulation is avoided, however, by undesired direct visual inspection of the implant through the large incision.

U.S. Pat. No. 4,013,690 describes a complex selfsuturing, endocardial pacemaker lead and a special integral handlestylet device permanently accompanying the lead from the time of manufacture. After the lead has been implanted using routine surgical technique, the handle activates the ejection of a thin, malleable wire through a distal tubular die and into the tissue. If the acute performance of the lead is satisfactory, the wire suture is broken at a predetermined separation point by means of rotation of the handle and the handle-stylet is removed. Any attempt the reposition this lead after this point would not be possible.

It is felt that this technology fails completely to provide a means to reverse the implant procedure and reposition the lead. Further, the violent contraction at defibrillation testing may weaken if not break the soft, malleable suture wire. Still further, as with '690, special and complex hardware is needed to accompany this lead.

U.S. Pat. No. 4,142,530 describes an epicardial pacemaker lead which is once again implanted through a significant incision in the patient's chest. Once positioned against the epicardium, the lead body is simultaneously pulled along and pressed onto the surface of the heart in order to engage the tissue in at least two curved pointed electrodes. This implantation requires the combination of lead retraction and compression by the surgeon. The means by which the compressive force is applied to the lead head is unclear. A straight, forward anchor is then activated by advancing a stylet against an internal feature of the anchor. This forward anchor generates a force which directs the curved electrodes against the tissue. A nylon wire is attached to the anchor to provide a means for the surgeon to retract the anchor.

It is felt that significant surgery would be necessary to implant such a device. Precise positioning of the electrode on the myocardium through a small incision may be difficult. Also, placement of a lead on the posterior side of the heart may be impossible. Accidental laceration of the myocardial circulation by either the pointed electrodes or the anchor feature seems likely. The presence of the nylon wire would slightly increase the dimensions of the lead body. This wire becomes an unused, and unnecessary component remaining in the lead and therefore in the patient after the implant.

U.S. Patent No. 4,233,991 discloses an endocardial electrode with a deployable helical hook. A provision is made to include a barb on these hooks. These leads are implanted using routine surgical technique. The first embodiment employs a nonreversible triggering element to deploy the hook. The second embodiment is deployed by means of a conically tipped stylet. Engagement of the heart tissue is accomplished by the application of external torque on the lead body by the surgeon.

It is felt that these devices fail to provide a means to reverse the implant procedure to accomplish repositioning or removal. Once either hook has been deployed, repositioning of the lead can be significantly hampered. Also, use of a barb may tear myocardial tissue due the contraction of the heart during defibrillation testing.

U.S. Pat. No. 4,357,946 teaches about an epicardial pacemaker lead which is to be implanted during thoracic surgery. Deployment of the helical screw fixation device is accomplished by means of rotation imparted by a stylet while the electrode head is in some fashion held upon the epicardial surface through an external force.

As with '128 and '530 above, it is felt that this technology fails to provide a device which can be implanted through a small incision. Moreover, a rotation action applied to the proximal end of a slim stylet is required to activate the fixation screw. The means to apply an external force to the lead head is unclear.

U.S. Pat. No. 4,378,023 discloses a percutaneously implanted myocardial electrode which blindly penetrates the myocardium to a significant depth. Fixation hooks are released within the myocardial tissue itself. External rotation is necessary to further deploy the fixation hooks. External traction is necessary to set the hooks into the tissue in at least one design.

It is felt that this technology fails on numerous counts. As with '530, precise placement of the electrode on the heart especially placement on posterior regions would be difficult if not impossible. Undesirable rotation of the lead to deploy the fixation hooks is required. Lead repositioning or removal would be extremely difficult. One embodiment in particular would require advancing the lead further into the myocardium to unset the hooks. Such a technique is completely blind and invites potentially lethal perforation of the heart.

U.S. Pat. No. 4,649,938 discloses an endocardial stimulating electrode which is implanted by means of routine surgical technique and requires the use of external rotation of the lead body to advance and attach helical screw to the tissue. Once fixed to the tissue, the spring-loaded helical screw holds the tissue in close proximity to the electrode.

It is felt that this technology fails to accomplish the goals of the instant invention because of the necessity to rotate the entire lead body to engage the tissue. Also, the combination of this undesirable lead body rotation and application of axial force to overcome the spring bias complicates the implant procedure.

U.S. Pat. No. 4,858,623 discloses an endocardial pacemaker lead which deploys a simple spring loaded hook from the lead by means of an axial force applied to an internal stylet. Once deployed, the lead engages tissue following application of external rotation imparted to the lead body. If repositioning is necessary, the stylet is further advanced to locate the hook in its most distal position. The lead is then pulled free of the tissue by simple traction.

If is felt that this technology fails to accomplish the goals of the instant invention because lead body rotation is necessary to attach the lead to the tissue. Also, as with '104, the ease of tissue disengagement by means of simple traction is an undesirable characteristic of a defibrillation lead.

SUMMARY OF THE INVENTION

The defibrillator electrode or electro-catheter of the instant invention is specifically designed for use as an internal defibrillator electrode, but also may be used as a pacing lead.

The instant invention incorporates fixation structure which is effective to hook engage adjacent tissue and to draw the adjacent tissue laterally into engagement with that portion of the electro-catheter from which the hook is supported, whether the fixation structure is carried by the distal end of the electrocatheter or an intermediate length portion of the electro-catheter.

The main object of this invention is to provide an electro-catheter which may be positioned using routine implant techniques including the use of an internal stylet or an outer tubular catheter, each of which being withdrawable to effect deployment of a resilient deformable distal end electrode of predetermined shape.

Another object of this invention is to provide an implantable and internally deployable defibrillation electrode including fixation structure which may be used to effect fixation of the electrode prior to internal deployment of the electrode.

Still another object of this invention is to provide an implantable and internally deployable defibrillation electrode including fixation structure which will allow for fixation of the deployable distal end of the electrode subsequent to deployment thereof.

Yet another important object of this invention is to provide an implantable defibrillation electrode fixation structure which may be actuated and deactuated merely through the utilization of a fixation stylet.

A further important object of this invention is to provide an implantable defibrillation electrode including fixation structure operative to engage adjacent tissue and to draw the distal end of the defibrillation electrode laterally into engagement with the engaged tissue.

Another important object of this invention is to provide an implantable defibrillation electrode including fixation structure which may be actuated by longitudinal force as opposed to rotary torque.

Still another object of this invention is to provide an implantable defibrillation electrode in accordance with the preceding object and incorporating a spring loading mechanism wherein the spring biasing action thereof accomplishes the fixation action and is more readily operable to release and subsequently reestablish fixation in the event it is desired to shift the positioning of a deployed defibrillation electrode subsequent to initial fixation thereof.

A final object of this invention to be specifically enumerated herein is to provide an implantable defibrillation electrode in accordance with the preceding objects and which will conform to conventional forms of manufacture, be of simple construction and easy to use so as to provide a device that will be economically feasible, long-lasting and relatively trouble free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a schematic fragmentary enlarged longitudinal vertical sectional view of the distal end of a deployable implantable defibrillation electrode constructed in accordance with the present invention and with the fixation structure thereof in a spring biased retracted position in solid lines and a partially extended position in phantom lines;

FIG. 5 is a schematic fragmentary enlarged longitudinal vertical sectional view similar to FIG. 1, but illustrating a third form of fixation device;

DETAILED DESCRIPTION OF THE PREFERRED EMBODIMENTS

Figure 2:
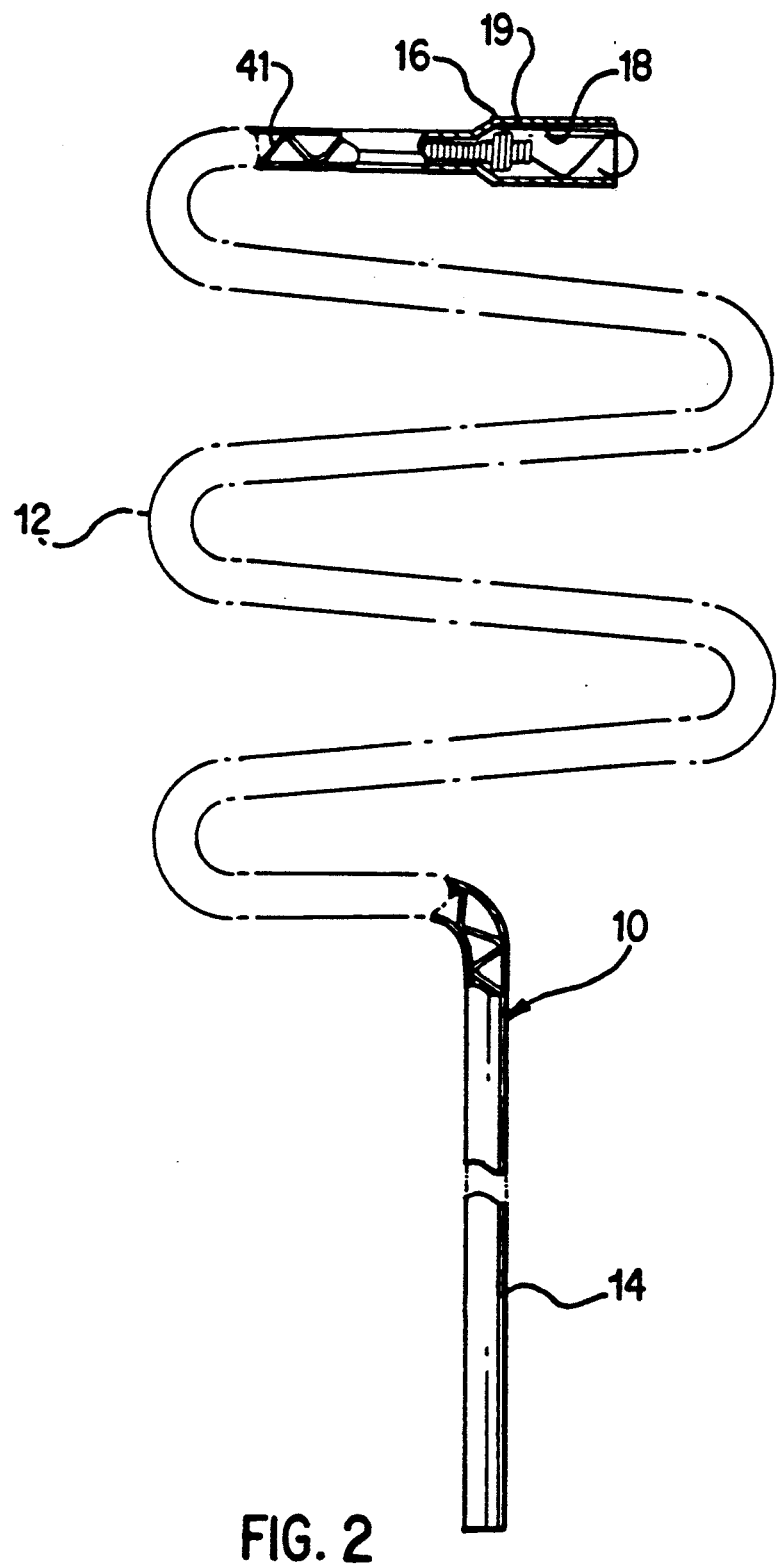
FIG. 2 is a schematic plan view of a first form of the deployed defibrillation electrode utilizing the fixation structure of FIG. 1.

Referring now more specifically to FIGS. 1 and 2 of the drawings, there may be seen an internally deployable electrocatheter referred to in general by the reference numeral 10 employing a deployable distal end portion 12 and a proximal end portion 14.

The distal end portion 12, in FIG. 2, is illustrated in its deployed preconfigured flat zig-zag shape, the entire length of the electro-catheter being flexible and the distal end portion 12 being capable of being straightened either through the use of an internal straightening stylet inserted thereinto from the proximal end portion 14 or an external flexible tubular catheter (not shown) of greater stiffness than the distal end portion 12.

The precise electrical construction of the deployable end portion 12 may be of any suitable well known type. Suffice it to say that through leads extending the length of the electrocatheter, electrical energy is delivered from a pulse generator to the cardiac tissue of the patient via the conductive distal end portion 12 of the structure.

The terminal distal end 16 comprises a dielectric (biocompatible polymer) tubular housing 19 and defines an endwise outwardly opening cylindrical cavity 18 into which the distal end 20 of a helical tubular spring 22 extending through the distal end portion 12 projects, the proximal end (not shown) of the spring 22 being anchored relative to the proximal end portion 14 in any convenient manner. The distal end 20 includes a stretchable diametrically enlarged portion 24 disposed within the cavity 18 terminating in a diametrically reduced terminal end 26 also disposed within the cavity 18. The portion 24 comprises axial thrust developing means for yieldingly biasing the terminal end 26 in one direction.

The base end 28 of a reverse turned spring hook 30 is anchored to the terminal end 26 of the spring 22 and includes a reversed turned hook 30 on its free end 32 substantially fully contained within the cavity 18.

After the electro-catheter has been inserted and positioned generally as desired for example the electro-catheter being inserted through the utilization of a tubular catheter, a fixation stylet (see FIG. 4B) is associated with the proximal end portion 14 and inserted through the electro-catheter 10 for engagement with the interior of the terminal end 26 of the spring 22 in which the base end 28 of the spring hook 30 is anchored. The fixation stylet thereafter is actuated against the terminal end 26 in a fashion similar to a camera cable release to force the latter toward the open end of the cavity 18 to and past the phantom line position thereof illustrated in FIG. 1 thus expanding the large diameter end portion 24 of the spring 22. Displacement of the terminal end 26 past the phantom line position of FIG. 1 projects the bend 23 of the reversed turned hook 32 from the open end of the cavity 18 for lateral displacement therefrom and engagement of the free end 32 thereof with the tissue to which the terminal distal end 16 is to be fixed. Then, the fixation stylet is released to enable retraction of the hook 30 from the phantom line position thereof to the solid line position thereof to thereby draw the exterior of the terminal distal end 16 laterally into tight contact with the tissue engaged by the hook 30.

Thereafter, the fixation stylet may be removed and the tubular catheter may be withdrawn from about the deployable end portion 12 to thereby enable the latter to deploy and assume the preconfigured shape thereof illustrated in FIG. 2.

Figure 3:
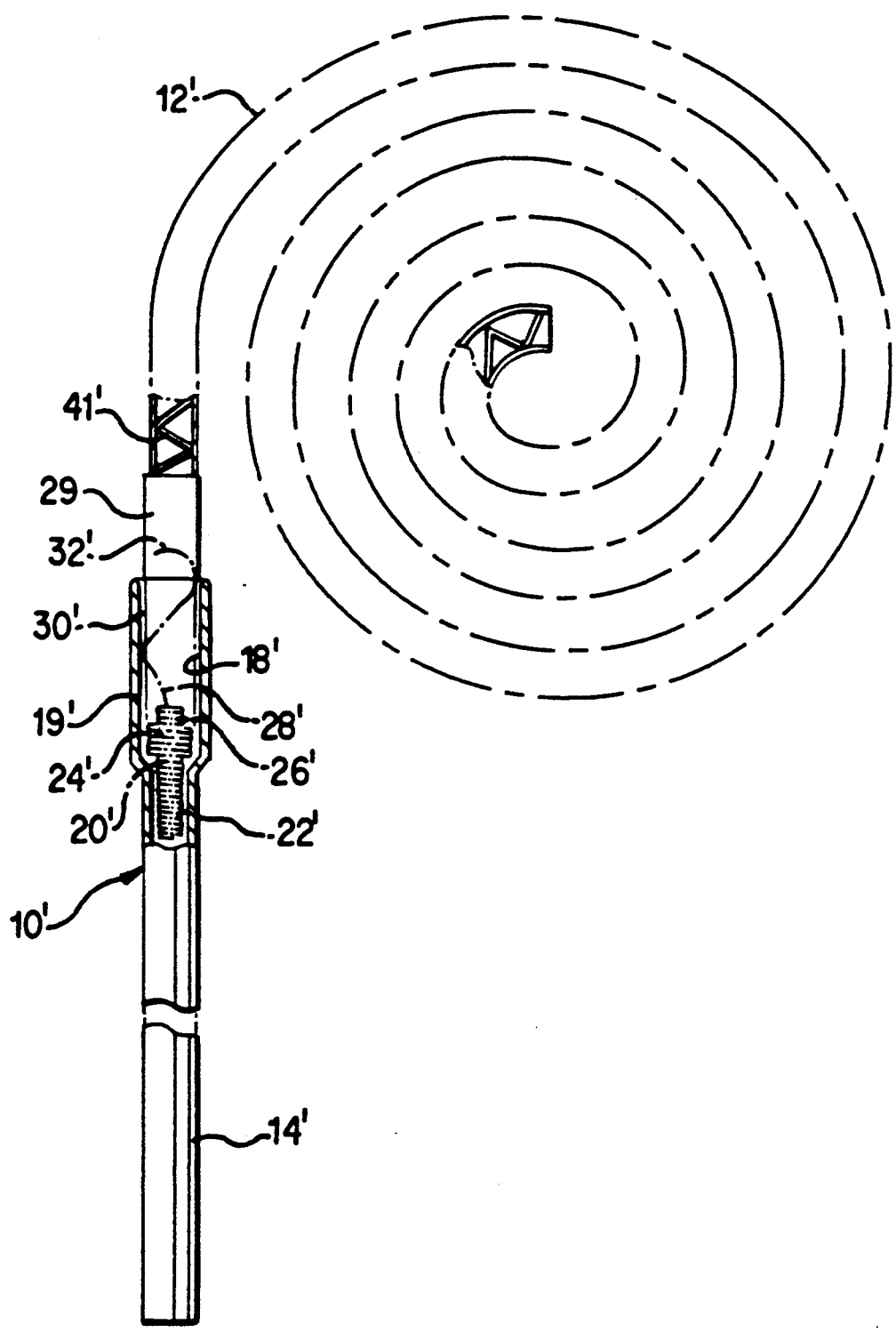
FIG. 3 is a schematic plan view of a second form implantable defibrillation electrode in a deployed condition and wherein the fixation structure of FIG. 1 is incorporated in an intermediate length portion of the electrode at the proximal end of the deployable distal end.

With attention now invited more specifically to FIG. 3, a modified form of electro-catheter is referred to in general by the reference 10' incorporating a deployable distal end portion 12' and a proximal end portion 14'. The electro-catheter 10' is of a design to be inserted through the utilization of a tubular catheter and the deployable distal end portion 12' thereof is in the form of a flat spiral coil.

The electro-catheter 10' incorporates a tubular housing 19' corresponding to the tubular housing 19 defining the cavity 18. The housing 19' is serially disposed within the electrocatheter 10' between the proximal end portion 14' thereof and the deployable distal end portion 12' thereof. The internal structure of the housing 19' is substantially identical to the internal structure of the housing 19 in that a helical tubular spring 22' corresponding to the spring 22 has its distal end 20' projecting into the cavity 18' of the housing 19' and the base end 28' of a spring hook 30' corresponding to the spring hook 30 is anchored in the terminal end 26' of the distal end 20', the distal end 20' including an enlarged diameter end portion 24' corresponding to the end portion 24.

The distal end portion 12' is, however, provided with a slot 29 through which the free end 32' of the spring hook 30' may be extended upon utilization of a fixation stylet, for example, of the camera shutter cable release type herein above referred to. Accordingly, the housing 19' of the electro-catheter 10' may be laterally anchored to suitable internal tissues through the utilization of a fixation stylet. In this manner, an intermediate portion of the electro-catheter 10' can be affixed to body tissue after the distal active end of the electrode is permitted to deploy into the preconfigured shape illustrated in FIG. 3.

Figure 4A:
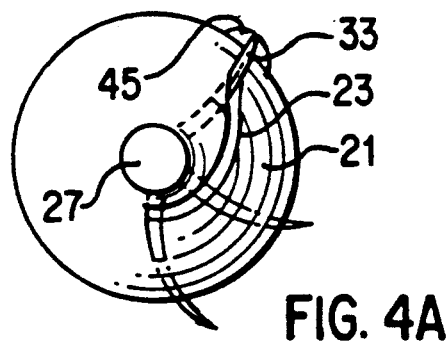
FIG. 4A is a distal end view of the structure illustrated in FIG. 4 with alternate positions of the fixation hook shown in phantom lines.
Figures 4, 4B:
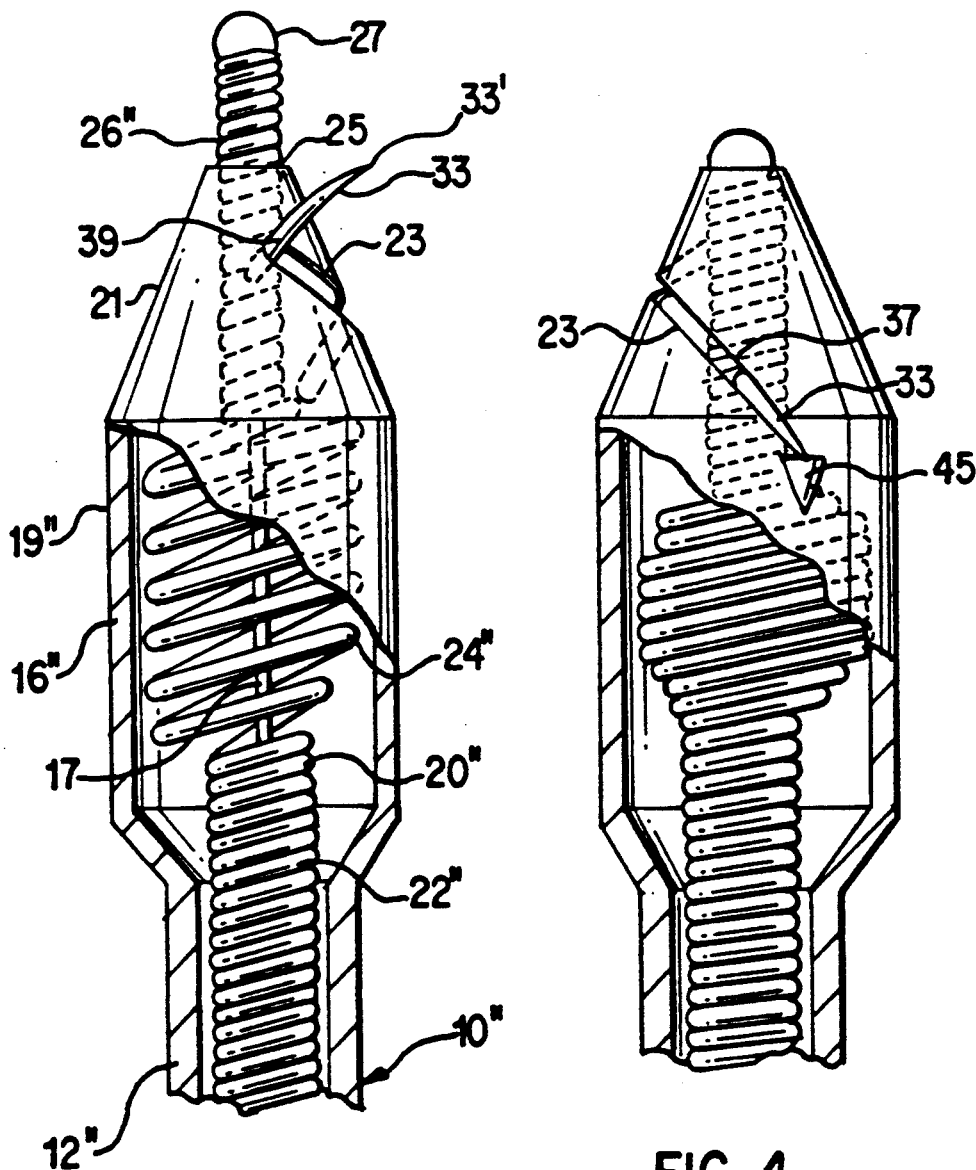
FIG. 4 is a side elevational view of a modified form of implantable defibrillation electrode fixation structure with portions of the tubular body of the electrode broken away and illustrated in section, the fixation hook thereof being in a retracted, shielded condition.
FIG. 4B is a fragmentary elevational view similar to FIG. 4 with the fixation hook being disposed in a fully extended position.

With attention now invited to FIGS. 4, 4A and 4B, there may be seen a terminal distal end 16" of an electro-catheter 10" which may be considered as substantially identical to the electrocatheter 10, except for the terminal distal end 16" thereof.

The electro-catheter 10" includes an internal coil spring 22" corresponding to the spring 20 equipped with a distal end 20" incorporating an enlarged diameter end portion 24" and a terminal end 26", all of which are enclosed with a housing 19", the distal terminal end of the housing 19" being hollow and frusto conical as at 21 and provided with a partial spiral slot 23. The terminal distal end of housing 19" is open as at 25 on its minor diameter end and the terminal end 26" is projectable through the open end 25 and includes an end enlargement 27 which is retractable only partly into the open end 25.

The terminal end 26" has the base end of a curved hook 33 anchored thereto and the hook 33 projects outwardly through and is slidably received within the slot 23, the slot 23 extending less than 180 degrees about the terminal distal end 21.

The housing 1911 may comprise the terminal distal end of an electro-catheter such as the electro-catheter 10 in lieu of the terminal distal end 19 thereof. The electro-catheter 10" would be designed for insertion in the same manner as the electrocatheter 10 and fixed in the desired position prior to deployment of the deployable distal end portion 12" of the electro-catheter 1011 corresponding to the deployable distal end portion 12.

In order to affix the terminal distal end 16", after the electro-catheter 10" has been positioned utilizing routine implant techniques such as a tubular delivery catheter, a fixation stylet 17, is inserted into the electro-catheter 10" and associated with the proximal end portion thereof. Then, the fixation stylet is operated in a fashion similar to a camera cable release to lengthwise elongate the enlarged diameter end portion 24" from the condition thereof illustrated in FIG. 4 to the expanded condition thereof illustrated in FIG. 4B, which movement causes the hook 33 to move from the end 37 of the slot 23 in which the hook 33 is retracted to the end 39 of the slot 23, in which position the hook 33 is fully extended, the terminal end 26" being projected through the open end 25 of the terminal distal end 21.

Thereafter, the fixation stylet may be released so that the spring biasing action of the enlarged diameter end portion 24" may retract the hook 33 back through the slot 23 from the end 39 thereof to the end 37 thereof, during which movement the hook 33 engages adjacent tissue and laterally draws the terminal distal end 21 toward and against that tissue and simultaneously draws the sharp point 33' into the outwardly opening recess 45 shown in FIG. 4.

After fixation of the electro-catheter 10", the tubular delivery catheter (not shown) may be withdrawn to thereby allow the distal end portion 12" to deploy and assume the preconfigured shape of the distal end portion 12 illustrated in FIG. 2.

The housings 19, 19' and 19" are insulated from the electrical conductors (not shown) which bring electrical energy to conductive outer surface portions of the distal end portions 12, 12' and 12". Further, the phantom lines 41 and 41' indicate the structure of the distal end portions 12 and 12', respectively, which comprise the spiral conductors disposed thereabout and which bring electrical energy to the outer surface portions of the end portions 12 and 12' (the electricity being supplied thereto through proximal lumen tubing or possible bilumen tubing with one lumen incorporating the electrical conductor leading to the conductors and the second lumen dedicated to operation of the fixation device). When the hook 33 is disposed in the end 37 of the slot 23 (subsequent to release of engagement of the hook 33 with organ tissue), it is positioned immediately forward of the shield 45 to thereby facilitate repositioning or removal of the electro-catheter 10" subsequent to its usage.

Figure 6:
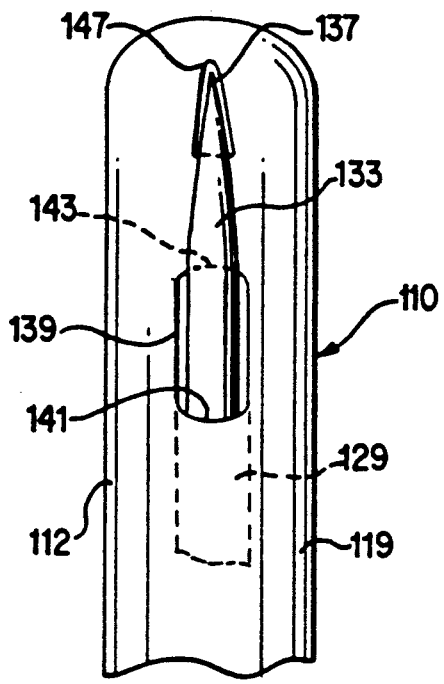
FIG. 6 is a fragmentary top plan view of the fixation device shown in FIG. 5.

With attention now invited more specifically to FIGS. 5 and 6, the numeral 110 generally designates an internally deployable electro-catheter similar to the electro-catheter 10 illustrated in FIGS. 1 and 2. All components of the catheter 110 corresponding to similar components of the catheter 10 are referred by similar reference numerals in the one hundred series. Distal end portion 112 includes a dielectric tubular housing 119 in which the distal end 120 of a helical tubular spring 122 is disposed. The distal end 120 includes a strengthable diametrically enlarged portion 124 disposed within a hollow cavity 118 formed in the housing 119 and the diametrically enlarged portion 124 terminates in a diametrically reduced terminal end 126 to which there is secured one end 127 of a thrust rod 129 through the utilization of a suitable fastener 121. The other end of the rod 129 has one end one 131 of a curved hook 133 pivotally secured thereto as at 135 and the free end of the hook 133 is pointed as at 137. The free end portion of the hook 131 projects through a radial opening 139 formed in the housing 119 and extending longitudinally thereof, the housing 119 including cam surfaces 141 and 143 at the proximal and distal ends, respectively, of the opening or slot 139.

The diametrically reduced terminal end 126 and the rod 129 may be advanced toward the rounded distal end 145 of the housing 19 in the same manner in which the terminal end 26 may be advanced from the solid line position thereof in FIG. 1 to the phantom line position thereof illustrated in FIG. 1.

When the rod 129 is in the retracted solid line position thereof illustrated in FIG. 5, the hook 133 is fully retracted and has its pointed end 137 received, within an outwardly opening notch 147 formed in one side of the distal end 145 of the housing 119. However, when the diametrically reduced portion 126 and the rod 129 are advanced toward the distal end 145, the cam surface 143 swings the hook 133 in a counterclockwise direction as viewed in FIG. 5 toward the lowermost extended position thereof illustrated in phantom lines. At this point, the housing 119 is positioned adjacent the pericardial sack and the diametrically reduced end portion 126 and the rod 129 are then allowed to retract toward the proximal end of the housing 119 where upon the hook 133 will hook engage the pericardial sack and swing toward the solid line position of the hook illustrated in FIG. 5 thereby fixing the housing 119 to the pericardial sack.

Figure 7:
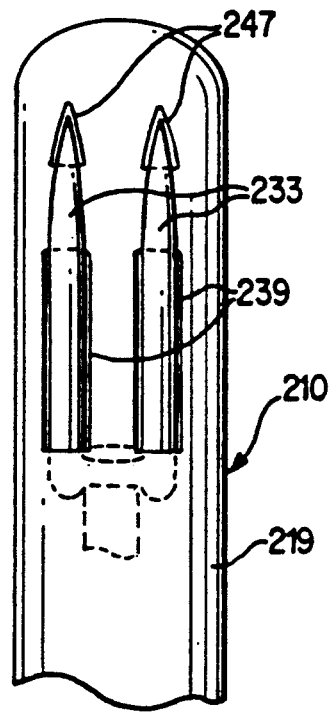
FIG. 7 is a fragmentary top plan view similar to FIG. 6, but illustrating a double hook form of the device shown in FIG. 6.

FIG. 6 illustrates the single hook 133 of the electrocatheter 110 illustrated in FIG. 5 and FIG. 7 illustrates a further modified form of electro-catheter 210 which is substantially identical to the electro-catheter 10, except that the electro-catheter 210 includes a pair of hooks or hook members 233 and a pair of recesses 247 in which to receive the free pointed ends of the hook members 233. In addition, the housing 219 of the electro-catheter 210 includes a pair radial openings or slots 239 through which the hooks or hook members 233 operate.

The use two hooks 233 as opposed to a single hook 133 merely provides additional assurance against dislodgement of the fixation device.

Of course, the fixation devices illustrated in FIGS. 5-7 may be incorporated either at the distal end of a deployable defibrillator end portion such as the end portion 12, or at the proximal end of a deployable end portion such as the end portion 12' illustrated in FIG. 3.

Figure 8:
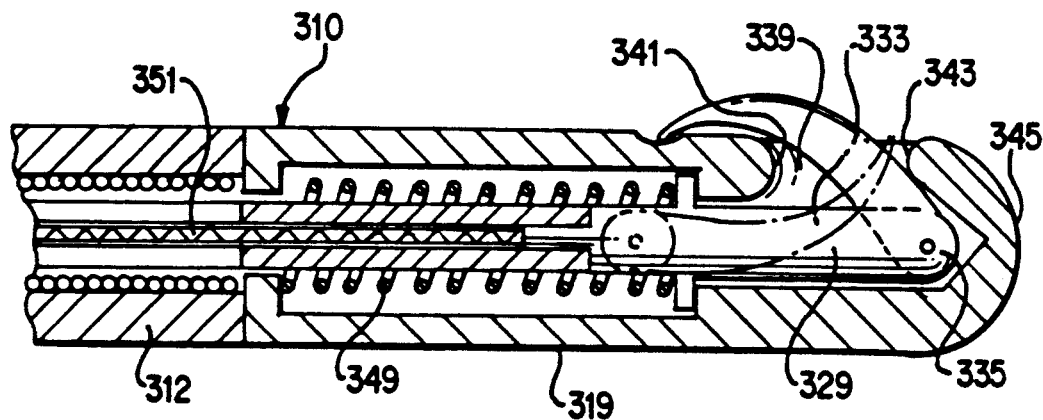
FIG. 8 is a schematic fragmentary enlarged longitudinal vertical sectional view similar to FIG. 5, but illustrating fifth form of fixation device incorporating a reverse swingable hook.

With attention now invited more specifically to FIG. 8, there may be seen yet a another form of deployable electrocatheter referred to in general by the reference numeral 310 including a deployable distal end portion 312. The deployable end portion 312 supports a tubular housing 319 therefrom including a radial slot or opening 339 terminating at cam surfaces 341 and 343 corresponding to the surfaces 141 and 143 and a rod 329 is reciprocal within the housing 319 corresponding to the rod 129 and has a hook or hook member 333 pivotally mounted from the distal end thereof as at 335. The rod 329 is yieldingly biased toward the distal end 345 of the housing 319 by a compression spring 349 and retracted away from the distal end 345 by a pull cord or the like 351. During movement of the rod 329 from the solid line position thereof to a position retracted fully away from the distal end portion 345, the hook 333 is cammed by the cam surface 341 to the phantom line position thereof illustrated in FIG. 8, and when the spring 349 is allowed to shift the rod 329 toward the distal end portion 345, the hook 333 is pivoted from the phantom line position thereof illustrated in FIG. 8 to the solid line position thereof. Of course, all of the fixation devices 110, 210 and 310 may be used on either the distal end portion 12 of the distal end portion 12'.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. An implantable defibrillation electrode comprising:
   an electro-catheter including a conductive distal end portion and a non-conductive proximal end portion, at least a major portion of the length of said distal end portion having a preconfigured shape and being resiliently deformable into a generally straight condition, said distal end portion including distal and proximal ends, at least one of said distal and proximal ends being hollow,
   hook means, shiftably supported in said at least one of said distal and proximal ends, for engaging body tissue and including a reversed turned free end portion and a mounted base end portion, said hook means further including a bend therein intermediate said free end portion and said base end portion contained within said hollow end when said hook means is in a retracted position and projectable outwardly of said hollow end when said hook means is in an extended position for lateral displacement of said hook means relative to said hollow end during final displacement of said hook means to said extended position,
   means for moving said hook means longitudinally of said electro-catheter from said retracted position, in which said hook means is at least substantially entirely contained within said hollow end, and said extended position, in which said hook means is substantially fully outwardly projected from said hollow end, and
   means for yieldingly biasing said hook means from said extended position toward said retracted position, and axial thrust developing means being slidingly telescoped through said proximal end portion and operatively associated with said hook means in order to exert an axial thrust thereon from a terminal end of said proximal end portion.

2. The electrode of claim 1 wherein said at least one of said distal and proximal ends comprises said distal end.

3. The electrode of claim 1 wherein said at least one of said distal and proximal ends comprises said proximal end.

4. An implantable defibrillation electrode comprising:
   an electro-catheter including a conductive distal end portion and a non-conductive proximal end portion, said distal end portion including distal and proximal ends, at least one of said distal and proximal ends being hollow,
   hook means, shiftably supported in said at least one of said distal and proximal ends, engaging body tissue and including a reversed turned free end portion and a mounted base end portion, said hook means further including a bend therein intermediate said free end portion and said base end portion contained within said hollow end when said hook means is in a retracted position and projectable outwardly of said hollow end when said hook means is in an extended position for lateral displacement of said hook means relative to said hollow end during final displacement of said hook means to said extended position,
   means for moving said hook means longitudinally of said electro-catheter from said retracted position, in which said hook means is at least substantially entirely contained within said hollow end, and said extended position in which said hook means is substantially fully outwardly projected from said hollow end, and
   means for yieldingly biasing said hook means from said extended position toward said retracted position, and axial thrust developing means being slidingly telescoped through said proximal end portion and operatively associated with said hook means in order to exert an axial thrust thereon from a terminal end of said proximal end portion.

5. The electrode of claim 4 wherein at least a major portion of the length of said distal end portion has a preconfigured shape and is resiliently deformably into a generally straight condition.

6. The electrode of claim 5 wherein said pre-configured shape comprises a spiral shape.

7. The electrode of claim 6 wherein said pre-configured shape comprises a generally flat spiral shape.

8. The electrode of claim 5 wherein said pre-configured shape comprises a generally flat zig-zag shape.

* * * * *